United States Patent
Ben-Yishai (10) Patent No.: US 10,482,614 B2
(45) Date of Patent: Nov. 19, 2019

(54) METHOD AND SYSTEM FOR REGISTRATION VERIFICATION

(71) Applicant: ELBIT SYSTEMS LTD., Haifa (IL)

(72) Inventor: Rani Ben-Yishai, Haifa (IL)

(73) Assignee: ELBIT SYSTEMS LTD., Haifa (IL)

(*) Notice: Subject to any disclaimer, the term of this patent is extended or adjusted under 35 U.S.C. 154(b) by 0 days.

(21) Appl. No.: 16/095,078

(22) PCT Filed: Apr. 19, 2017

(86) PCT No.: PCT/IL2017/050458
§ 371 (c)(1),
(2) Date: Oct. 19, 2018

(87) PCT Pub. No.: WO2017/183032
PCT Pub. Date: Oct. 26, 2017

(65) Prior Publication Data
US 2019/0108645 A1   Apr. 11, 2019

(30) Foreign Application Priority Data

Apr. 21, 2016  (IL) .......................................... 245339

(51) Int. Cl.
*G06T 7/33* (2017.01)
*G06T 7/73* (2017.01)
(Continued)

(52) U.S. Cl.
CPC .............. *G06T 7/337* (2017.01); *A61B 34/10* (2016.02); *A61B 34/20* (2016.02); *A61B 90/37* (2016.02);
(Continued)

(58) Field of Classification Search
CPC .................................................... G06T 7/337
(Continued)

(56) References Cited

U.S. PATENT DOCUMENTS 5,678,546 A * 10/1997 Truppe ..................... A61B 5/06
                                                    128/898
5,740,802 A *  4/1998 Nafis ................... G06F 19/3481
                                                    600/407
(Continued)

FOREIGN PATENT DOCUMENTS

EP       2 233 099 A2    9/2010
EP       2 676 627 A2   12/2013
WO    WO 2014/139019 A1    9/2014

OTHER PUBLICATIONS

"Head Mounted Displays for Medical Use" Kurtis Keller, May 30, 2014.*
(Continued)

*Primary Examiner* — Javid A Amini
(74) *Attorney, Agent, or Firm* — Knobbe, Martens, Olson & Bear, LLP (57) ABSTRACT

Method for verifying registration of a model of an internal-body-part with the internal-body-part in a reference coordinate system. The internal-body-part is at least partially unseen directly by a user. The method includes the procedures of continuously determining a position and orientation of a head-mounted-display in the reference coordinate system, determining a display location of at least one virtual marker, and displaying the virtual marker according to the display location. The display location of the virtual marker is determined according to the expected position of a respective at least one reference point relative to the head-mounted-display. The reference point is directly visible to the user. The relative position between the reference point and the internal-body-part is substantially constant. The position of the reference point in the reference coordinate system is predetermined. When the model and the internal-body-part are effectively registered, the reference point and corresponding virtual marker appears visually in alignment.

26 Claims, 7 Drawing Sheets

(51) Int. Cl.
*G06T 11/60* (2006.01)
*A61B 90/00* (2016.01)
*A61B 34/20* (2016.01)
*A61B 34/10* (2016.01)
*A61B 90/50* (2016.01)

(52) U.S. Cl.
CPC ............... *G06T 7/75* (2017.01); *G06T 11/60* (2013.01); *A61B 2034/105* (2016.02); *A61B 2034/2057* (2016.02); *A61B 2034/2074* (2016.02); *A61B 2090/363* (2016.02); *A61B 2090/365* (2016.02); *A61B 2090/372* (2016.02); *A61B 2090/373* (2016.02); *A61B 2090/395* (2016.02); *A61B 2090/3945* (2016.02); *A61B 2090/502* (2016.02); *G06T 2207/30204* (2013.01)

(58) Field of Classification Search
USPC ........................................................ 345/633
See application file for complete search history.

(56) References Cited

U.S. PATENT DOCUMENTS

| | | | | |
|---|---|---|---|---|
| 5,765,561 | A * | 6/1998 | Chen | G09B 23/28 |
| | | | | 348/77 |
| 5,912,720 | A * | 6/1999 | Berger | A61B 3/145 |
| | | | | 351/206 |
| 6,351,573 | B1 * | 2/2002 | Schneider | G06F 19/321 |
| | | | | 382/128 |
| 6,891,518 | B2 * | 5/2005 | Sauer | G02B 27/017 |
| | | | | 345/8 |
| 7,190,331 | B2 | 3/2007 | Genc et al. | |
| 7,491,198 | B2 | 2/2009 | Kockro | |
| 8,737,708 | B2 | 5/2014 | Hartmann et al. | |
| 2002/0107522 | A1 * | 8/2002 | Picard | A61B 17/15 |
| | | | | 606/88 |
| 2007/0018975 | A1 | 1/2007 | Chuanggui et al. | |
| 2007/0083107 | A1 | 4/2007 | Ferre et al. | |
| 2008/0243142 | A1 * | 10/2008 | Gildenberg | G16H 50/50 |
| | | | | 606/130 |
| 2009/0003512 | A1 * | 1/2009 | Pouliot | A61B 6/466 |
| | | | | 378/4 |
| 2009/0088830 | A1 * | 4/2009 | Mohamed | A61F 2/91 |
| | | | | 623/1.11 |
| 2011/0015649 | A1 | 1/2011 | Anvari et al. | |
| 2011/0080996 | A1 * | 4/2011 | Paidi | G06T 11/006 |
| | | | | 378/21 |
| 2011/0257653 | A1 * | 10/2011 | Hughes | A61B 34/10 |
| | | | | 606/79 |
| 2012/0068913 | A1 * | 3/2012 | Bar-Zeev | G02B 26/026 |
| | | | | 345/8 |
| 2013/0090547 | A1 * | 4/2013 | Bani-Hashemi | A61N 5/1039 |
| | | | | 600/411 |
| 2013/0121457 | A1 * | 5/2013 | Maltz | A61B 6/032 |
| | | | | 378/4 |
| 2014/0078517 | A1 * | 3/2014 | Ben-Yishai | A61B 8/4254 |
| | | | | 356/614 |
| 2015/0016680 | A1 | 1/2015 | Mack et al. | |
| 2015/0305701 | A1 * | 10/2015 | Wendler | G01T 1/161 |
| | | | | 600/436 |
| 2017/0091554 | A1 * | 3/2017 | Miyamoto | G06T 11/60 |

OTHER PUBLICATIONS

Fischer et al. "Model-based Hybrid Tracking for Medical Augmented Reality" Eurographics Symposium on Virtual Environments (2006) The Eurographics Association 2006.

Kawanishi et al. "A 3D registration method for surgery navigation system of total knee arthroplasty", the Institute of Electronics, Information and Communication Engineers, IEICE Technical Report MI200/-182 (20096-01).

Rowena E. Ong, "Intra-Operative Registration Methods for Image-Guided Kidney Surgery", Submitted to the Faculty of the Graduate School of Vanderbilt University.

Richard Lee Holloway, "Registration Errors in Augmented Reality Systems", A dissertation submitted to the faculty of the University of North Carolina at Chapel Hill. 1995.

Hideyuki Suengaga, Real-time in situ three-dimensional integral videography and surgical navigation using augmented reality: a pilot study. International Journal of Oral Science, 2013, 5.2: pp. 98-102.

International Search Report dated Jul. 30, 2017 for International Application No. PCT/IL2017/050458, 8 pages.

Written Opinion of the International Searching Authority dated Jul. 30, 2017 for International Application No. PCT/IL2017/050458, 5 pages.

* cited by examiner

METHOD AND SYSTEM FOR REGISTRATION VERIFICATION

CROSS REFERENCE TO RELATED APPLICATIONS

This application the U.S. National Phase Application under 35 U.S.C. § 371 of International Application No. PCT/IL2017/050458, filed Apr. 19, 2017, designating the U.S., which claims priority to Israeli Application No. IL 245339, filed on Apr. 21, 2016, the entire disclosure of each of which is hereby incorporated by reference.

FIELD OF THE DISCLOSED TECHNIQUE

The disclosed technique relates to registration of coordinate systems in general, and to methods and systems for verifying registration of a model of an internal body part with the internal body part, in a reference coordinate system, where the internal body part is unseen directly by a user, during visor guided procedures in particular.

BACKGROUND OF THE DISCLOSED TECHNIQUE

When performing an image-guided procedure, a monitor displays for the user a model of a body part and a model of a medical tool, both registered in a reference coordinate system. The tool is being tracked relative to a reference unit rigidly attached to the body or fixed relative thereto. If the reference unit accidently moves, the model of the tool is displayed at an erroneous position and orientation relative to the model of the body part. When performing visor guided procedures, a model of the relevant body part is displayed to the user on the visor at a perspective corresponding to the position and orientation of the user relative to the relevant body part, such that the model appears to the user to be at the position and orientation of the body part. Specifically, in minimally invasive visor guided procedures, the user sees a representation of an internal body part (i.e., a model of the internal body part) where other body parts are perceived by the user to be transparent, and the user may perform the procedure without exposing the internal body part. To that end, the model is registered with the relevant body part (i.e., the position and orientation associated with the model corresponds to the position and orientation of the internal body part in a reference coordinate system). However, if the model and the internal body part fall out of registration, the user may be presented with erroneous information regarding to the position and orientation of the internal body part. One prior art technique for verifying registration during image-guided procedures employs intra-operative imaging (e.g. X-ray images or live fluoroscopy using a C-arm) presented on a monitor. The surgeon verifies that the position of the tool, as captured in the intra-operative images and presented in real-time on a monitor, corresponds to the position of the tool relative to the internal body part as it appears in the monitor of the image-guiding system, preferably from more than one perspective. Another prior art technique includes placing the tracked tool at selected locations on the body part that are visible by the surgeon and that also appear in the model of the body part, and confirming that the model of the tool is displayed on the monitor of the image-guiding system at the corresponding position on the model of the body part. Both techniques may interfere with the surgical workflow, distract the surgeon and lengthen the surgery, which may lead, among others, to an increased probability of infection.

P.C.T Application Publication 2014/139019 to Sela et al, entitled "System and Method for Dynamic Validation, Correction or Registration for Surgical Navigation" directs in one embodiment therein, to an overlay of a visualization of a tracked instrument and patient imaging information, on a video image provided during a procedure. According to the method directed to by Sela et al, any registration errors may be recognized by a user as a simple misalignment of the instrument visualization and the actual physical instrument seen on the video image.

SUMMARY OF THE PRESENT DISCLOSED TECHNIQUE

It is an object of the disclosed technique to provide a novel methods and system for a method and system for verifying registration of a model of an internal body part with the internal body part in a reference coordinate system.

In accordance with the disclosed technique, there is thus provided a method for verifying registration of a model of an internal body part with the internal body part in a reference coordinate system. The internal body part is at least partially unseen directly by a user. The method includes the procedures of continuously determining a position and orientation of a head mounted display in the reference coordinate system, determining a display location of at least one virtual marker, and displaying the at least one virtual marker according to the display location. The display location of the at least one virtual marker is determined according to the expected position of a respective at least one reference point relative to the head mounted display. The at least one reference point is directly visible to the user. The relative position between the at least one reference point and the internal body part is substantially constant. The position of the at least one reference point in the reference coordinate system is predetermined. When the model and the internal body part are effectively registered, the at least one reference point and corresponding at least one virtual marker appears visually in alignment.

According to another aspect of the disclosed technique, there is thus provided a system for verifying registration of a model of a body part with the internal body part in a reference coordinate system. The body part is at least partially unseen directly by a user. The system includes a head mounted display to be donned by the user, a head mounted display tracking module and a processor coupled with the head mounted display tracking module. The head mounted display tracking module continuously determines information relating to the position and orientation of the head mounted display in the reference coordinate system. The processor determines the position and orientation of the head mounted display in the reference coordinate system. The processor further determines the display location of at least one virtual marker according to the position of a respective at least one reference point relative to the head mounted display. The reference point is visible to the user. The relative position between the at least one reference point and the body part is substantially constant. The position of the at least one reference point in the reference coordinate system is predetermined. The processor renders the at least one virtual marker to be displayed on the head mounted display. When the model and the body part are effectively registered, the at least one reference point and the corresponding virtual marker are displayed on the head mounted display visually in alignment.

According to a further aspect of the disclosed technique, there is thus a method for verifying registration of a model of an internal body part with the internal body part in a reference coordinate system. The internal body part is at least partially unseen directly by a user. The method includes the procedures of acquiring an image of at least one reference point from a known position and orientation in the reference coordinate system, identifying the at least one reference point in the acquired image and determining the image location of the at least one reference point. The method further includes the procedures of determining the expected image location of at least one reference point and determining the congruence between the predicted and determined image location of the at least one reference point. The at least one reference point is directly visible to the user. The relative position between the at least one reference point and the internal body part is substantially constant. The position of the at least one reference point in the reference coordinate system is predetermined. The expected image location of at least one reference point is determined according to the position of the at least one reference point and the position and orientation from which the image was acquired in the reference coordinate system. When the model and the internal body part are registered, the predicted and determined image locations are congruent with each other.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a method and a system for verifying registration of a model of an internal body part with the internal body part, in a reference coordinate system. The internal body part is unseen directly by a user. The term 'unseen directly' by a user or a camera or an optical detector, refers to herein that an unobstructed Line Of Sight (LOS) does not exist between an object and the user or the camera or the optical detector. Conversely, the terms 'directly seen' or 'directly visible' by a user or a camera or an optical detector refers to herein that an unobstructed LOS exists between the object and the user or the camera or the optical detector. According to the disclosed technique, at least one reference point is determined, the point being directly visible to said user. The relative position between the reference point and the internal body part is substantially constant. The position of the at least one reference point in said reference coordinate system is predetermined. Furthermore, the position and orientation, abbreviated herein 'P&O', of a Head Mounted Display (HMD) relative to a reference tracking unit which is fixed relative to the internal body part, is continuously determined. Thus, the relative positions and orientations, abbreviated herein 'P&Os', between the HMD and the reference points are also continuously determined. At least one virtual marker corresponding to the at least one reference point is displayed on the HMD. As long as the relative position between the reference tracking unit and the internal body part does not change (i.e., the model and the internal body part are registered), the at least one reference point and the corresponding displayed virtual marker appear to the user to be in visual alignment. When the model and the internal body part are effectively not registered, the at least one reference point and the corresponding displayed virtual marker appear to the user to be out of visual alignment. Thus, the user is provided with a visual indication that the model and the internal body part are not registered. Accordingly, the user may visually verify throughout the procedure (i.e., without interrupting the procedure workflow) that the model and the internal body part are indeed registered. It is noted that the terms 'effectively fall out of registration', 'effective miss-registration', 'effectively miss-registered', 'effectively not-registered' and 'effectively out of registration' are used herein interchangeably and are further defined herein below in conjunction with FIG. 2. It is further noted that the disclosed technique is applicable to any kind of procedure in which the internal body part is unseen or partially unseen directly by the user, such that the user cannot verify that the displayed model is perceived as aligned correctly with the body part. As such, the technique is also applicable to open procedures. It is further noted that the term 'visor' used herein relates in general to optically see-through displays such as smart glasses, augmented reality glasses, near-to-eye displays, head mounted displays and head wearable displays. Such see-through displays may be based on technologies such as visor projection, combiners, waveguide technologies (e.g., microstructure extraction, diffractive optics or holograms, micro-mirrors beam-splitter, polarization reflection), retinal scanning, on-pupil optics or contact lenses and the like.

Figure 1A:
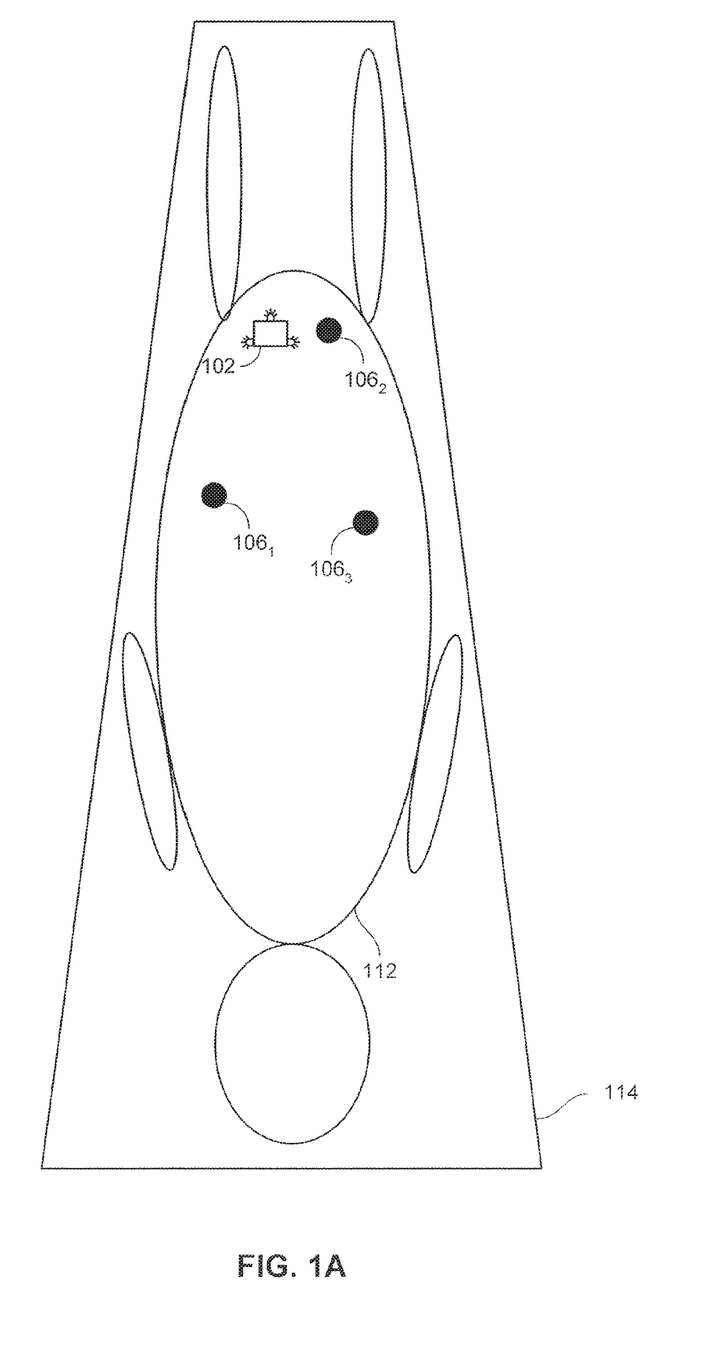
FIGS. 1A, 1B, 1C and 1D are schematic illustrations of registration verification of a model of an internal body part with the internal body part, in a reference coordinate system, operative in accordance with an embodiment of the disclosed technique.
Figure 1B:
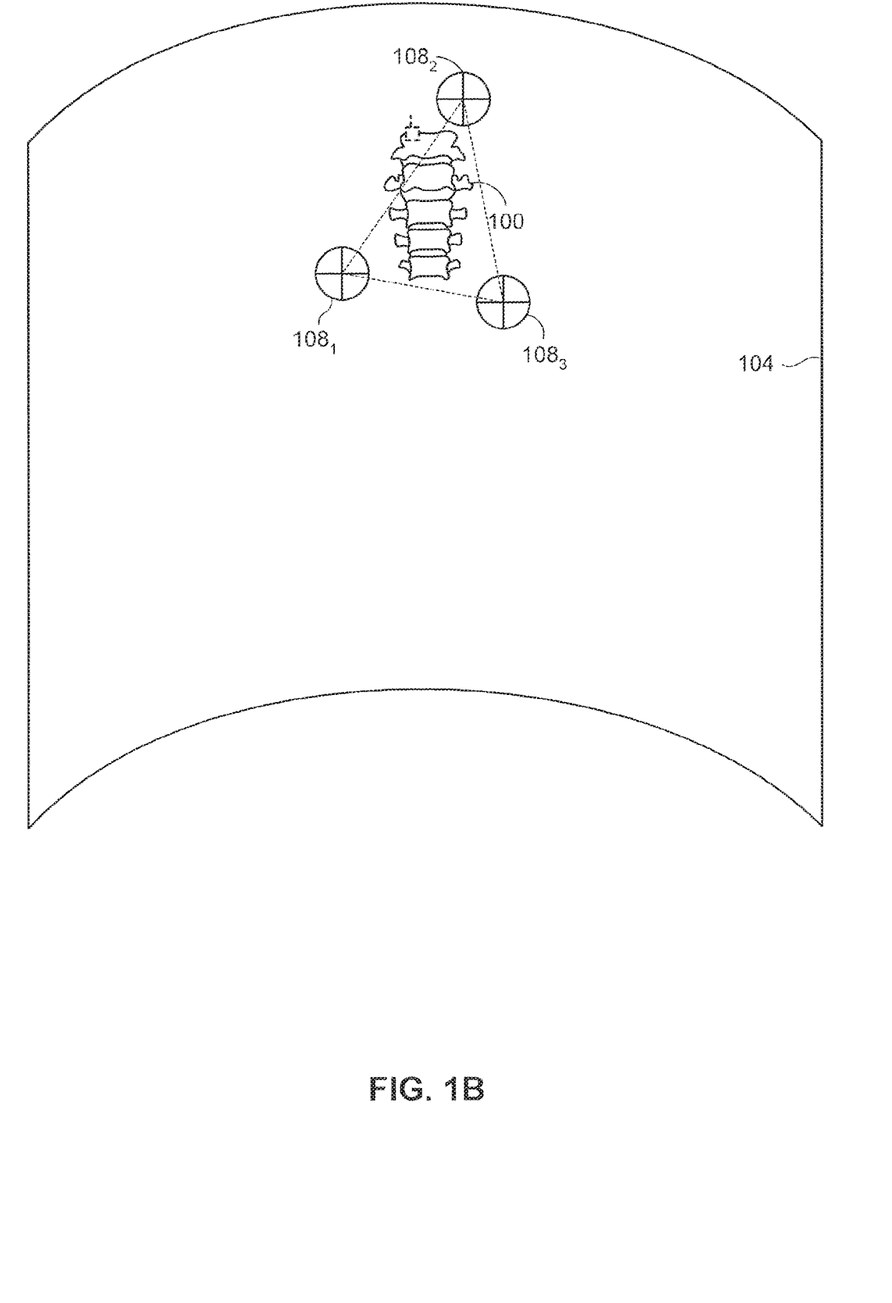
Figure 1C:
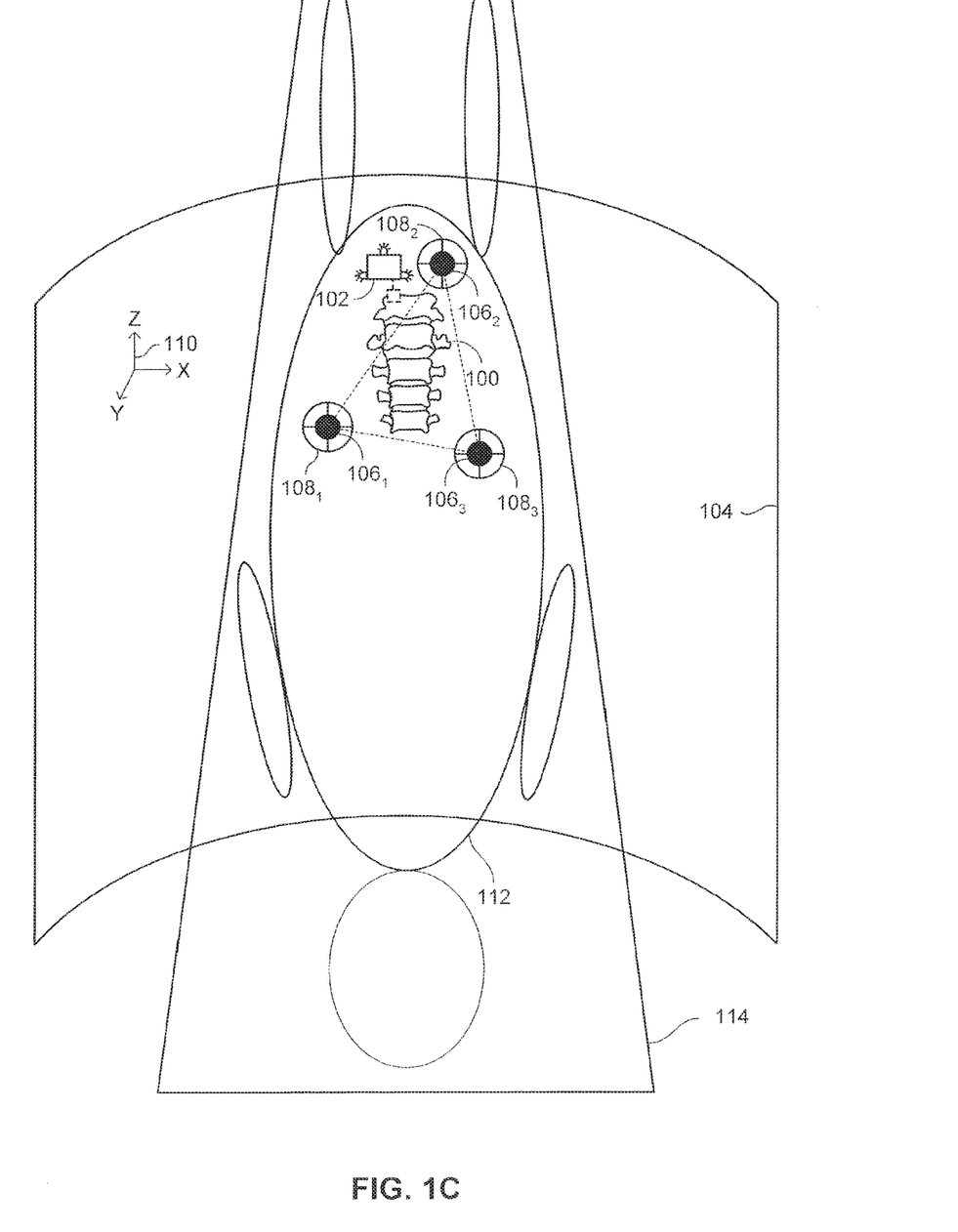
Figure 1D:
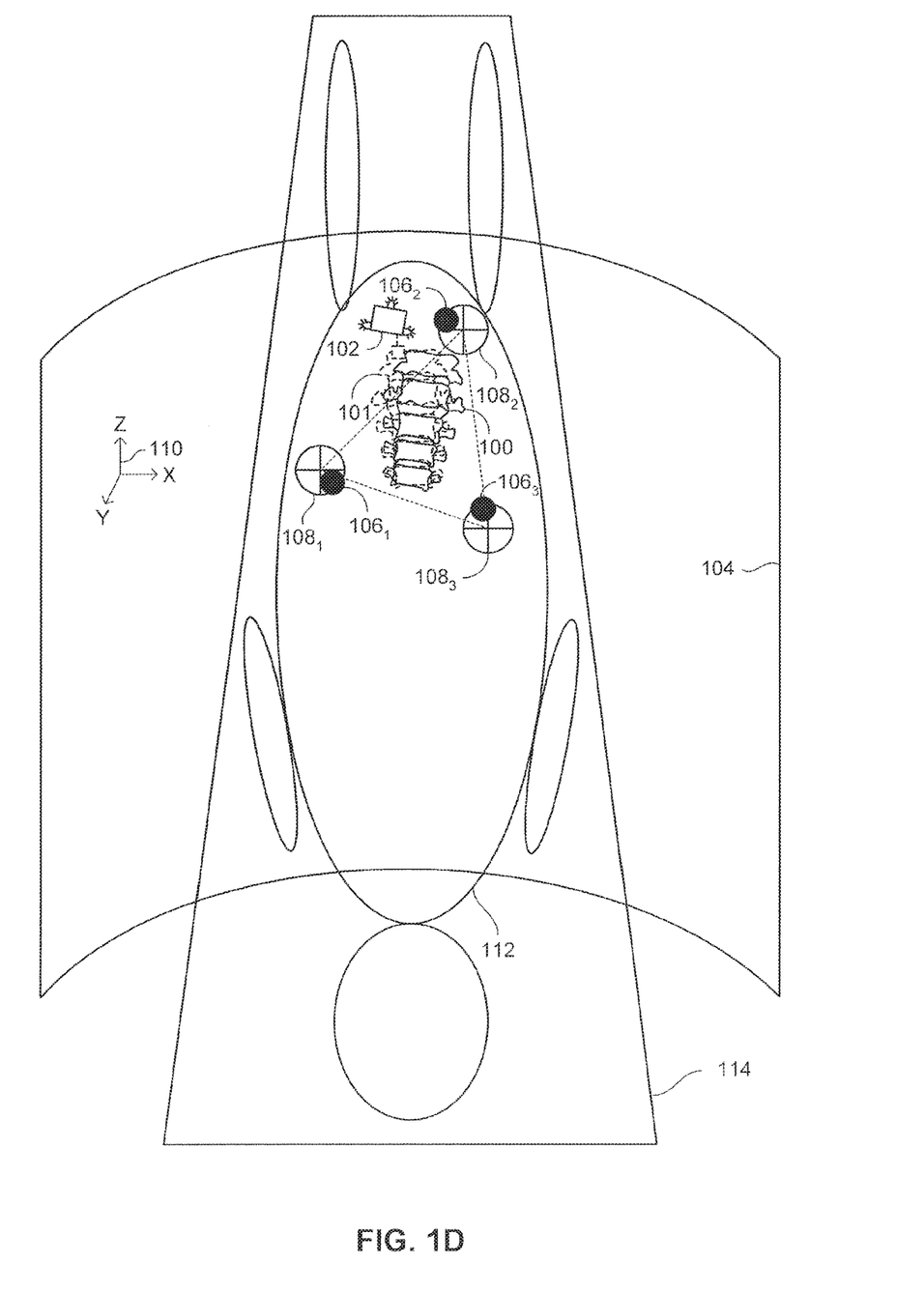

Reference is now made to FIGS. 1A, 1B, 1C, and 1D, which are schematic illustrations of registration verification of a model 100 of an internal body part 101 with internal body part 101, in a reference coordinate system 110 operative in accordance with an embodiment of the disclosed technique. FIG. 1A illustrate the physical objects (i.e., the "real world") observed by a user. These physical objects are patient 112 lying on treatment bed 114 as well reference points $106_1$, $106_2$ and $106_3$ and reference tracking unit 102. FIG. 1B illustrates a visor 104 (a physical object) and the virtual objects displayed on visor 104. These virtual objects are virtual markers $108_1$, $108_2$ and $108_3$ and a virtual perspective of model 100 of the internal body part. FIGS. 1C and 1D illustrate the view point of a user looking at a patient through a see-through HMD display, such as visor 104, which displays a virtual perspective of model 100 and virtual markers $108_1$, $108_2$ and $108_3$. Internal body part 101 is unseen directly by the user (i.e., as indicated by the hatched line in FIG. 1D). Initially, a reference tracking unit 102 is fixedly placed relative to internal body part 101 such that the relative P&O between reference tracking unit 102 and internal body part 101 is substantially constant. Reference tracking unit 102 defines reference coordinate system 110. Thereafter, the P&O of reference tracking unit 102 is determined relative to internal body part 101, as further elaborated below. In other words, the P&O of internal body part 101, in reference coordinate system 110 is determined. Furthermore, the P&O of model 100 in reference coordinate system 110 is determined also as further explained below. Thus, model 100 of internal body part 101 is registered with the respective internal body part 101 thereof.

During a medical procedure, a patient 112 lies on a treatment bed 114, and the P&O of the HMD relative to reference tracking unit 102 is continuously determined. Consequently, the tracking system determines the P&O of the HMD relative to internal body part 101. Thus, model 100 may be rendered in the correct perspective and displayed, for example, on visor 104 of the HMD.

However, during the medical procedure, model 100 may effectively fall out of registration with respective internal body part 101, for example, when reference tracking unit 102 is accidently moved. Thus, the relative P&O between reference tracking unit 102 and internal body part 101 has changed. However, the registered position of model 100 relative to reference tracking unit 102 does not change with the motion thereof. As such model 100 is no longer registered with respective internal body part 101. Consequently, the user may be displayed with erroneous information with respect to the P&O of internal body part 101 without any indication thereof.

According to the disclosed technique, at least one reference point directly visible to a user is determined within the field of view of the user. In the example brought forth in FIGS. 1A-1D, three reference points $106_1$, $106_2$ and $106_3$, directly visible to the user, are determined within the field of view of the user. The relative position between reference points $106_1$, $106_2$ and $106_3$ and internal body part 101 is substantially constant. Reference points $106_1$, $106_2$ and $106_3$ may be markings marked by the user, for example, with a marker (e.g., on the skin of patient 112). Reference points $106_1$, $106_2$ and $106_3$ may also be markers (e.g., adhesive markers) attached to patient 112 or to treatment bed 114. As a further example, these reference points may be prominent features (e.g., screw heads) of a fixture with a substantially fixed spatial relation (i.e., a fixed P&O) relative to body part 101 (e.g. a Mayfield clamp holding the head during head surgery). Reference points $106_1$, $106_2$ and $106_3$ may further be prominent anatomical features which are directly visible to the user such as the outside corner of the eye, a tooth or the surface of a thigh. In general, the term 'reference point' relates herein to a point, surface or object that is directly visible to the user, where the position of the reference point, relative to internal body part 101, is substantially constant and the position thereof, in reference coordinate system 110, can be determined either manually or automatically as further elaborated below in conjunction with FIG. 2.

The position of reference points $106_1$, $106_2$ and $106_3$, in reference coordinate system 110 (i.e. relative to reference tracking unit 102) is determined (e.g., by placing the tip of a tracked wand on reference points $106_1$, $106_2$ and $106_3$) prior to the onset of the procedure (i.e., the position of reference points $106_1$, $106_2$ and $106_3$ is predetermined). As mentioned above, the relative positions between reference points $106_1$, $106_2$ and $106_3$ and internal body part 101 are substantially constant. In general, when the reference points are located on the skin of the patient, the relative position may momentarily change, for example, when the reference tracking unit is attached to a vertebra and the surgeon applies force to puncture the vertebral bone with an awl. However, once the surgeon stops applying force, the original relative positions are restored.

Since the P&O of the HMD relative to reference tracking unit 102 is continuously determined during the procedure, the expected positions of reference points $106_1$, $106_2$ and $106_3$ relative to the HMD are also continuously determined (i.e. the P&O of the HMD relative to the positions of reference points $106_1$, $106_2$ and $106_3$ in coordinate system 110, as determined at the beginning of the procedure). During the procedure, an image of model 100 rendered from the determined perspective of the HMD and three virtual markers $108_1$, $108_2$ and $108_3$ corresponding to reference points $106_1$, $106_2$ and $106_3$, are displayed to the user donning the HMD. The system continuously updates the rendered image of model 100 and determines the display location of the rendered image and the display location of each one of virtual markers $108_1$, $108_2$ and $108_3$ (i.e., the display locations at which the rendered image of model 100 and virtual markers $108_1$, $108_2$ and $108_3$ should be displayed). The display locations are determined according to the P&O of the HMD and the expected position of reference points $106_1$, $106_2$ and $106_3$ relative to the HMD as further explained below. Accordingly, virtual markers $108_1$, $108_2$ and $108_3$, corresponding to reference points $106_1$, $106_2$ and $106_3$, are displayed on the HMD, aligned with the expected location of reference points $106_1$, $106_2$ and $106_3$ relative to the HMD, when observed by the user looking through visor 104.

When the relative position between reference tracking unit 102 and reference points $106_1$, $106_2$ and $106_3$ and between reference tracking unit 102 and internal body part 101 does not change (i.e., model 100 and the internal body part 101 are registered), virtual markers $108_1$, $108_2$ and $108_3$ are displayed in visual alignment (FIG. 1A) with the corresponding reference points $106_1$, $106_2$ and $106_3$. In addition to visually verifying the registration, when several body parts that can move one relative to the other are involved, the visual alignment of reference points $106_1$, $106_2$ and $106_3$ and the corresponding virtual markers $108_1$, $108_2$ and $108_3$ provides the surgeon with an indication that the displayed model of the body part may be relied on. In such cases, applying force on one body part may move the body part relative to other body parts, and may also momentarily move the tracker reference unit that is attached to one of the body parts.

If, for example, reference tracking unit 102 accidently moves, the relative position between reference tracking unit 102 and reference points $106_1$, $106_2$ and $106_3$ and between reference tracking unit 102 and internal body 101 part changes as well (i.e., model 100 and the internal body 101 part effectively fall out of registration). However, virtual markers $108_1$, $108_2$ and $108_3$ are displayed on the HMD according to the originally determined relative position between reference tracking unit 102 and reference points $106_1$, $106_2$ and $106_3$. Thus, reference points $106_1$, $106_2$ and $106_3$ and the corresponding virtual markers $108_1$, $108_2$ and $108_3$ are displayed out of alignment (FIG. 1D) and the user may visually detect (i.e., without any action and with no interruption to the workflow of the procedure) that model 100 and the internal body part 101 are not registered. Also, the distance between the reference points and the corresponding virtual markers, as perceived by the user looking through visor 104, may indicate the level of miss-registration between model 100 and the internal body part 101.

In FIGS. 1C and 1D, each one of virtual markers $108_1$, $108_2$ and $108_3$ corresponds to a respective one of reference points $106_1$, $106_2$ and $106_3$. However, virtual markers $108_1$, $108_2$ and $108_3$ may be replaced with a geometrical shape (e.g., a polygon, a circle, an ellipse and the like), where reference points $106_1$, $106_2$ and $106_3$ are located on the perimeter of the geometrical shape. For example, virtual markers $108_1$, $108_2$ and $108_3$ may be replaced with a triangle where each vertex corresponds to one of reference points $106_1$, $106_2$ and $106_3$, as illustrated by the hatched triangle in FIG. 1C. According to another example, when four reference points are employed, the virtual marker may be a square were each vertex corresponds to one of the reference points. According to yet another example, the virtual marker may be a single marker (i.e., similar to one of virtual markers $108_1$, $108_2$ and $108_3$), which is alternately associated with each of the reference points for a predetermined period of time. In general, at least one virtual marker is associated with at least one of the at least one reference point for at least a portion of the time (e.g. all virtual markers are blinking or turned on and off by the user). When one of reference points $106_1$, $106_2$ and $106_3$ is, for instance, a tooth, the virtual marker may take the form of an outline of the tooth as seen from the current perspective of the user. When the reference point is, for instance, the surface of a thigh, the virtual marker may take the form of a wireframe wrapping the thigh or two lines overlaying the edges of the thigh, as seen from the current perspective of the user.

Figure 2:
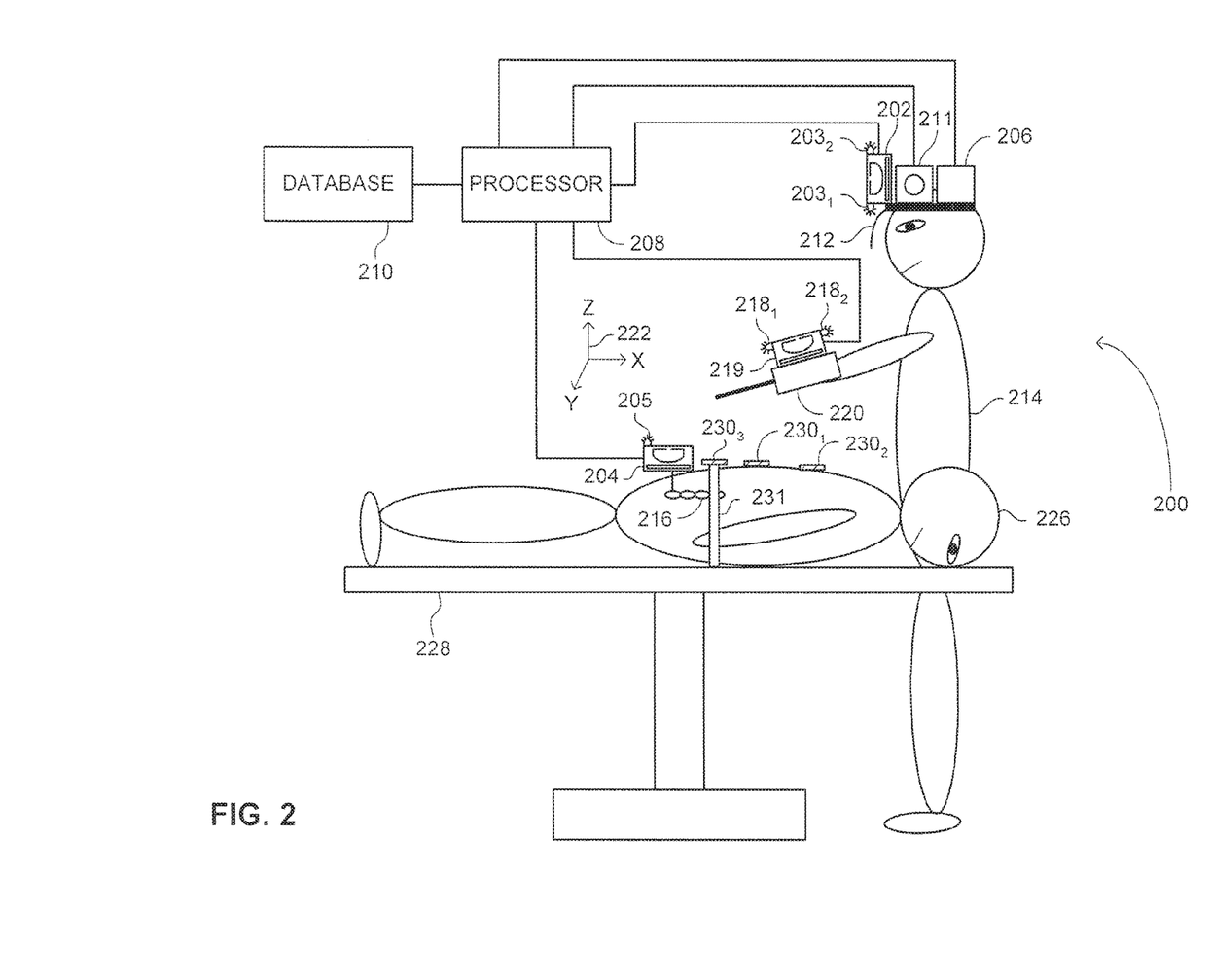
FIG. 2 is a schematic illustration of a system for verifying registration of a model of an internal body part with the internal body part in a reference coordinate system, constructed and operative in accordance with another embodiment of the disclosed technique.

Reference is now made to FIG. 2, which is a schematic illustration of a system, generally referenced 200, for verifying registration of a model of an internal body part with the internal body part in a reference coordinate system, constructed and operative in accordance with another embodiment of the disclosed technique. System 200 includes an HMD tracking unit 202, a reference tracking unit 204, an HMD 206, a processor 208 and a database 210. System 200 optionally includes an interrogation camera 211, the connectivity and functionality of which is elaborated below. HMD 206 includes a see through display 212. HMD tracking unit 202 is fixedly attached to HMD 206. Reference tracking unit 204 defines a reference coordinate system 222, and is fixedly placed relative to internal body part 216 such that the relative P&O between reference tracking unit 204 and internal body part 216 is substantially fixed. System 200 optionally includes a tool tracking unit 219 attached to a medical tool 220 (e.g., a needle, a pointer, a medical power drill and the like).

Processor 208 is coupled with database 210, with HMD tracking unit 202, with HMD 206, with reference tracking unit 204 and with tool tracking unit 216. HMD 206 along with HMD tracking unit 202 is intended to be donned by a user 214. As mentioned above, reference tracking unit 204 is attached to internal body part 216 of patient 214 or fixed relative thereto, such that the relative P&O between reference tracking unit 204 and the internal body part 216 is substantially fixed. Internal body part 216 is, for example, a vertebra, the cranium and brain, the mandible or a femur. Similar to as mentioned above, internal body part 216 is unseen directly by user 214 (i.e., an unobstructed LOS does not exist between user 214 and internal body part 216). System 200 is associated with a reference coordinate system 222 which, in the system 200 is also the coordinate system associated with reference tracking unit 204. Patient 226 is lying on treatment bed 228.

HMD tracking unit 202 and reference tracking unit 204 define an HMD tracking module, which along with processor 208 define an HMD tracking system which tracks the P&O of HMD 206 relative to reference tracking unit 204 (i.e., in reference coordinate system 222). Tool tracking unit 219 and reference tracking unit 204 define a tool tracking module, which along with processor 208 define a tool tracking system which tracks the P&O of tool 220 relative to reference tracking unit 204 (i.e., in reference coordinate system 222). In the example brought forth in FIG. 2, both the HMD tracking system and the tool tracking system exhibit an in-out-out-in configuration. As such, HMD tracking unit 202 includes an optical detector and at least two emitters $203_1$ and $203_2$. Reference tracking unit 204 includes at least one optical detector and further includes at least one emitter 205 (i.e., a reference emitter). Reference tracking unit 204 may include two or more optical detectors and two or more emitters, thereby increasing the field of view thereof. Tool tracking unit 219 also includes an optical detector and at least two emitters $218_1$, $218_2$. It is noted that light emitters 205, $203_1$, $203_2$, $218_1$ and $218_2$ may each be a light source or a light reflector.

When tracking HMD 206 in reference coordinate system 222, HMD tracking unit 202 acquires an image or images of emitter 205 and provides these images to processor 208. Also reference tracking unit 204 acquires an image or images of emitters $203_1$ and $203_2$ and provides these images to processor 208. These acquired images include information relating to the P&O of HMD 206 in reference coordinate system 222. Processor 208 determines the P&O of HMD 206 relative to reference tracking unit 204 according to these acquired images. It is noted that since processor 208 determines the P&O of HMD 206 based the information relating to the P&O included in the acquired images, the determined P&O of HMD 206 may differ from actual P&O of HMD 206 (e.g., due to partial obstruction of light emitters or optical detector lenses). Similarly, when tracking tool 220 in reference coordinate system 222, tool tracking unit 219 acquires an image or images of emitter 205 and provides these images to processor 208. Reference tracking unit 204 acquires an image or images of emitters $218_1$ and $218_2$ and provides these images to processor 208. These images include information relating to the P&O of tool 220 in reference coordinate system 222. Processor 208 determines the P&O of tool 220 relative to reference tracking unit 204 according to these acquire images. Similar to as described above, since processor 208 determines the P&O of tool 220 based the information relating to the P&O included in the acquired images, the determined P&O of tool 220 may differ from actual P&O of tool 220.

During the procedure, HMD 206 displays on visor 212 a model of body part 216 at a perspective corresponding to the position and orientation of user 214 relative to internal body part 216, such that user 214 perceives the model to be located at the P&O of internal body part 216. The model may be one-dimension (1D), two-dimensional (2D) or three-dimensional (3D). A 1D model is, for example, a single point that was determined by the surgeon as the target destination for inserting a needle or another instrument (e.g. the point is the center of a tumor when planning a brain biopsy, or a chosen point in a brain ventricle when planning the insertion of a shunt). The surgeon may determine this point at the beginning of the procedure, for instance by employing a cursor on a screen showing an MRI image data set of the brain. The term 'image data set' relates herein to collection of images of the body part. The surgeon may also determine an entry point and a trajectory which may also be displayed. An example for a 2D model is a single slice rendered from a 3D image data set. Such a 3D image data set may be, for example, a collection of two-dimensional CT or MRI axial slices also referred to herein as 'imageries'. The single rendered slice may be axial, coronal, sagittal or oblique. The surgeon can select which slice to display and change the selected slice during the procedure, for instance by using a user-interface as further describe below. Alternatively, the user may point a tracked wand at the desired slice level (i.e., relative to body part 216) and the corresponding slice is displayed (i.e., according to the position of the tip of the tracked wand). A 3D model is, for example, a segmentation of the image representation of body part 216, generated before or at the beginning of the procedure from a 3D image data set. A 3D model may also be a volume rendering visualization of a 3D image data set, generated dynamically from the 3D image data set according to the P&O of HMD 206 in reference coordinate system 222. In such a case, the registration is determined between the 3D image data set from which the volume rendering is generated and body part 216 and thus with reference coordinate system 222.

In general, when the image data set (i.e., the slice images) is registered with reference coordinate 222, all the models or visualizations that are derived therefrom will also be registered with reference coordinate 222. Registration of a model of a body part with body part 216 relates herein also to the registration of the image data set that the model is based on, or was generated from, with body part 216. The model may be generated from the raw data via an automatic process, a manual process or a mixed process (e.g. automatic segmentation, manual segmentation or automatic segmentation and manual fine-tuning of the segmentation). Also, the model may comprise the image data set without any processing. The model may be based on pre-acquired images or intra-operative images. These pre-acquired or intra-operative images may be for instance Computer Tomography (CT) images, Magnetic Resonance Imager (MRI) images, ultrasound images, Proton Emission Tomography (PET) images and the like. A 3D ultrasound image data set may be generated by a tracked 2D or 3D ultrasound transducer used intra-operatively.

To display a model of body part 216 at a perspective corresponding to the P&O of user 214 relative to internal body part 216 (i.e., such that user 214 perceives the model to be located at the P&O of internal body part 216), a model of internal body part 216 (i.e., generated from pre-acquired or intra-operative images of internal body part 216) should be registered with internal body part 216. Accordingly, at the onset of a medical procedure, a model of internal body part 216 is registered with internal body part 216. To register a model of internal body part 216 with internal body part 216, the P&O of internal body part 216 is determined in reference coordinate system 222.

According to one exemplary alternative for registering pre-acquired imageries of internal body part 216 with internal body part 216, a tracked C-Arm X-ray imager acquires at least two 2D X-ray images of internal body part 216 at two different positions and orientations relative to internal body part 216 in reference coordinate system 222. In other words, the C-Arm X-ray imager acquires at least two images of internal body part 216 from at least two different perspectives. The P&O of the C-arm imager is tracked in reference coordinate system 222, hence the P&Os from which the images are acquired (i.e., also in reference coordinate system 222) may be determined, as further described below. Thereafter, processor 208 determines a P&O of the pre-acquired imageries which corresponds with the at least two acquired 2D X-ray images (i.e. processor 208 determines the P&O of the pre-acquired imageries in reference coordinate system 222, or equivalently the P&O of internal body part 216 in reference coordinate system 222, which are consistent with the X-ray images of internal body part 216). When internal body part 216 includes several body parts (e.g. bones) that can move one relative to the other, processor 208 may determine the P&O of each body part separately. For example, when internal body part 216 is the spine, processor 208 may determine the P&O of each vertebra separately. This is required if the pre-acquired images were acquired when the patient was lying in one position, whereas during the surgery the patient is lying in another position and therefore, each vertebra may exhibit a different relative P&O.

The P&Os from which the X-Ray images are acquired in reference coordinate system 222 are determined similarly to as described above with respect to HMD 206 and tool 220. To that end, an imager tracking unit is fixedly placed on the imager at a known P&O relative to the imager coordinate system. This imager tracking unit is coupled with processor 208 and includes an optical detector and at least two emitters. The imager tracking unit acquires an image or images (i.e., tracking images employed for tracking) of emitter 205 at each of the at least two perspectives, and provides these images to processor 208. Reference tracking unit 204 acquires an image or images (i.e., also tracking images employed for tracking) of the emitters of the imager tracking unit and provides these images to processor 208. The images acquired by the imager tracking unit and reference tracking unit 204 include information relating to the P&O of the imager coordinate system (i.e., since the imager tracking unit is fixedly placed on the imager at a known P&O relative to the imager coordinate system) in reference coordinate system 222. Processor 208 determines the P&O of the X-ray imager coordinate system according to the images acquired by reference tracking unit 204 and the imager tracking unit.

According to one exemplary alternative for registering intra-operative imageries with internal body part 216, a tracked 3D imager acquires intra-operative 3D image data. An imager tracking unit is fixedly attached to the 3D imager at a known P&O relative to the imager coordinate system. Hence, the P&O of the imager coordinate system in reference coordinate system 222 may be determined directly. The P&O of the imager coordinate system in reference coordinate system 222 is determined as described above. Consequently, the P&O of the 3D image data can directly be determined in reference coordinate system 222.

As mentioned above, during the medical procedure internal body part 216 and the model thereof may effectively fall out of registration, for example if tracking reference unit 204 accidently moves from its original P&O. Thus, the relative P&O between reference tracking unit 204 and internal body part 216 changes. However, the registered position of the model relative to reference tracking unit 204 does not change with the motion thereof. As such the model is no longer registered with respective internal body part 216. As another example, HMD 206 moves relative to the head of user 214. Consequently the relative position between visor 212 and the eyes of user 214, which was calibrated prior to the onset of the procedure, changes. However the model is rendered according to the original relative position between visor 212 and the eyes of user 214. Thus, the model is displayed at an erroneous perspective and display position on visor 212 relative to the eyes of user 214 HMD 206 may include a sensor for tracking the location of the eye, and movements of HMD 206 relative to the head of user 214 may be automatically compensated for, and consequently, in such a case, the model will not effectively fall out of registration even when the HMD moves relative to the head. As a further example, when the tracking system is an optical tracking system, emitter 205 may be partially obscured from HMD tracking unit 202 (e.g., due to splattering of blood thereon) or the aperture of the optical detector of reference tracking unit 204 may partially covered. Similarly, light emitters $203_1$ and $203_2$ may be partially obscured from reference tracking unit 204 or the aperture of the optical detector of HMD tracking unit 202 may partially covered. Thus, either the images of light emitter 205 acquired by the HMD tracking unit 202, the images of light emitters $203_1$ and $203_2$ acquired by the reference tracking unit 202, or both may include erroneous information regarding the relative P&O between HMD tracking unit 202 and reference tracking unit 204. The model of internal body part 216 may be rendered according to this erroneous relative P&O between HMD tracking unit 202 and reference tracking unit 204. Thus, the model is displayed at an erroneous perspective and display position on visor 212. It is noted that the terms 'effectively fall out of registration', 'effective miss-registration', 'effectively not-registered', herein above and below relate to at least one of the above mentioned events of movement of reference unit 204 from the original P&O thereof, movement of HMD 206 relative to the head of user 214 and any other events which cause erroneous display, such as emitter 205 being partially obscured from HMD tracking unit 202 or the aperture of optical detector of reference tracking unit 204 being partially covered. When other tracking technologies are employed, as further elaborated below, the falling out of registration may be caused by other respective issues. For example, when the tracking system is an electromagnetic tracking system, the introduction or motion of a metallic object in the vicinity of the tracking system may result in the falling out of registration.

When internal body part 216 and the model thereof effectively fall out or registration, user 214 may be presented with erroneous information regarding the position of internal body part 216. To aid user 214 in verifying the registration between internal body 216 and the model thereof and to detect when they effectively fall out of registration, according to the disclosed technique, at least one reference point, directly seen by user 214, is determined within the field of view of user 214. In the example brought forth in FIG. 2, three reference points $230_1$, $230_2$ and $230_3$, directly seen by user 214, are determined within the field of view of user 214. The relative position between reference points $230_1$, $230_2$ and $230_3$ and internal body part 216 is substantially constant. Reference points $230_1$, $230_2$ and $230_3$ may be markings marked by user 214, for example, with a marker (e.g., on the skin of patient 226 or on treatment bed 228). Reference points $230_1$, $230_2$ and $230_3$ may also be markers (e.g., adhesive markers) attached to patient 226. As a further example, reference points $230_1$, $230_2$ and $230_3$ may be prominent features (e.g., screw heads) of a fixture with a fixed spatial relation (i.e., a fixed P&O) relative to the body part, or anatomical features similar to as mentioned above. In FIG. 2, reference points $230_1$, $230_2$ are exemplified as markers attached to patient 226 and reference point $230_3$ is exemplified as attached to a fixture 231 attached to bed 228 (e.g., a fixture to which a retractor is attached). The positions of reference points $230_1$, $230_2$ and $230_3$, relative to reference tracking unit 204, and thus in reference coordinate system 222 are determined prior to the onset of the procedure (i.e., the positions of reference points $230_1$, $230_2$ and $230_3$ are predetermined).

To determine the positions of reference points $230_1$, $230_2$ and $230_3$ relative to reference tracking unit 204 (i.e., and thus relative to internal body part 216), user 214 employs a tracked pointer (i.e., tool 220 is a tracked pointer) and places the tip of the tracked pointer on each one of reference points $230_1$, $230_2$ and $230_3$. Processor 208 determines the P&O of tool 220 in reference coordinate system 222 as described above, and further determines the position of the tip of tool 220 according to a known relative position between tool tracking unit 219 and the tip of tool 220. User 214 may instruct the system to determine the P&O of tool 220 and determine the position of a reference point via a user interface as described below.

According to another alternative, the user moves around reference points $230_1$, $230_2$ and $230_3$ through at least two positions. Each position is associated with a respective viewing angle of the reference point. At each viewing angle, the user designates each one of reference points $230_1$, $230_2$ and $230_3$ by aiming the head such that a cross, which is displayed in the center of the visor 212, aligns with each of reference points $230_1$, $230_2$ and $230_3$, and instructing the system (via a user interface) to determine the P&O of HMD 206 while doing so. For each viewing angle, processor 208 determines position related information respective of each one of reference points $230_1$, $230_2$ and $230_3$ according to the P&O of HMD 206. The position related information includes respective directions toward each of reference points $230_1$, $230_2$ and $230_3$. Each direction defines a line in reference coordinate system 222. The intersection of the at least two lines associated with each reference points $230_1$, $230_2$ and $230_3$ defines the location of that reference point in reference coordinate system 222. The above mentioned user interface may be, for example, one of a touchscreen operated by non-sterile staff, a sterile tablet (e.g., covered with nylon), and a menu that appears on visor 212 that may be controlled, for example, via a sterile wireless remote control or a pedal.

According to yet another alternative, the pre-acquired or intra-operative imageries of internal body part 216 may include, in addition to the representation of internal body part 216, representations of reference points $230_1$, $230_2$ and $230_3$ in the form of fiducial markers or prominent anatomical features. For example, when the internal body part is the skull or inner parts of the head, pre-acquired MRI imageries may also include the patient's eyes, specifically the canthi (i.e. the corners of the eyes). The canthi may be employed as reference points, for instance during an Ear Nose and Throat (ENT) procedure. According to another example, when the internal body part is the femur, the imageries may also include a representation of the surface of the thigh which may be used as a reference surface. In such cases, user 214 may mark these reference points on the image data set, for example, with the aid of a pointer on a display. These reference points (or reference surface) may also be automatically identified using image processing. For example, when the reference points are adhesive radio-opaque fiducial markers, they can be automatically identified in CT imageries by image processing. Since the model is registered with internal body part 216, each position in the imageries has a corresponding position in reference coordinate system 222. Thus, Processor 208 determines the position of each one of reference points $230_1$, $230_2$ and $230_3$ in reference coordinate system 222 and relative to reference tracking unit 204.

As mentioned, the relative position between reference points $230_1$, $230_2$ and $230_3$ and reference tracking unit 204 is known and expected to stay substantially constant throughout the procedure. Also as mentioned above, processor 208 continuously determines the P&O of HMD tracking unit 202 relative to reference tracking unit 204. Thus, processor 208 continuously determines the expected positions of reference points $230_1$, $230_2$ and $230_3$ relative to HMD tracking unit 202. Processor 208 determines the display location of each one of the virtual markers (e.g., virtual markers $108_1$, $108_2$ and $108_3$—FIG. 1) corresponding to reference points $230_1$, $230_2$ and $230_3$, according to the expected position of reference points $230_1$, $230_2$ and $230_3$ relative to HMD tracking unit 202, according to the known P&O between HMD tracking unit 202 and visor 212 and the known position of the eye of user 214 relative to HMD 206. Processor 208 may further determine the expected perspective of each one of reference points $230_1$, $230_2$ and $230_3$. Processor 208 renders the virtual markers (e.g., virtual markers $108_1$, $108_2$ and $108_3$—FIG. 1) according to the expected perspective and display location and provides an image of the rendered virtual markers to HMD 206 and HMD 206 displays this image to user 214.

The virtual markers are displayed on HMD 206 according to the originally determined relative position between reference tracking unit 204 and reference points $230_1$, $230_2$ and $230_3$, according to the relative P&O between reference tracking unit 204 and HMD tracking unit 202, and according to the position of the eye of user 214 relative to HMD 206. When internal body part 216 and the model thereof are effectively registered, reference points $230_1$, $230_2$ and $230_3$ and the corresponding virtual markers thereof are displayed in visual alignment. However, when internal body part 216 and the model thereof effectively fall out of registration, for instance when reference tracking unit 204 is moved or the determined relative P&O between reference tracking unit 204 and HMD tracking unit 202 is erroneous, the virtual markers are displayed out of alignment with respect to reference points $230_1$, $230_2$ and $230_3$, and user 214 may visually detect that internal body part 216 and the model thereof are effectively not registered. Also, when HMD 206 moves relative to the head and thus the eyes of user 214, the relative P&O between visor 212 and the eyes of user 214 changes and the virtual markers are displayed out of alignment with respect to reference points $230_1$, $230_2$ and $230_3$.

When user 214 identifies that internal body part 216 and the model thereof effectively fall out of registration, the system may aid user 214 to determine the source of the effective miss-registration and rectify the problem. For example, the system may request user 214 to validate the relative position between the eye thereof and HMD 206, by holding tool 220 in front of HMD 206 and viewing a virtual model of tool 220 displayed on visor 212. Processor 208 determines the P&O of tool 220 relative to HMD 206 using tool tracking unit 219 and HMD tracking unit 202 and displays the model of tool 220 accordingly. When user 214 indicates to the system that the virtual model of tool 220 is not aligned with tool 220, the system notifies user 214 that the problem may be that HMD 206 has moved relative to the head of user 214 or that at least one of emitters $203_1$ and $203_2$ and the optical detector in HMD tracker unit 202 might be partially obscured (e.g., by blood splatter). If the problem persists after cleaning the optical detector in HMD tracker unit 202 or emitters $203_1$ and $203_2$, the system may request the user to calibrate the current eye position, for instance by using a special calibration jig.

According to another scenario, when reference tracking unit 204 includes more than one optical detector, the system may instruct user 214 to move around patient 226 to check whether the virtual marker or markers appear visually out of alignment with reference points $230_1$, $230_2$ and $230_3$, while tracking with at least one other detector in reference tracking unit 204 (i.e. the system may notify the user which optical detector is currently in use, for instance via a message displayed on visor 212). If the virtual marker or markers appear in visual alignment with reference points $230_1$, $230_2$ and $230_3$, when tracking with at least one other detector in reference tracking unit 204, this may indicate that the first detector was partially obscured. If the virtual marker or markers still appear out of visual alignment with reference points $230_1$, $230_2$ and $230_3$ when tracking with at least one other detector in reference tracking unit 204, then this may indicate that the reference tracking unit 204 has moved. The nature of such a movement may be that reference tracking unit 204 can be returned to its original position (e.g., when the adaptor that holds the reference tracking unit 204 has several discrete states or when the adaptor has one degree of freedom which is more inclined to move). In such a case, the system may instruct user 214 to move reference tracking unit 204 while continuously checking if the problem is solved. This can potentially obviate the need for re-registering (i.e., thus saving the time required by the registration process).

According to another embodiment of the disclosed technique, processor 208 automatically detects effective miss-registration between internal body part 216 and the model thereof (i.e., without the involvement of the user). According to one option, a camera acquires an image from the point of view of the user. The image includes real-world features (e.g., reference points $230_1$, $230_2$ and $230_3$) and virtual features (e.g., the virtual markers) as seen by the user. The camera is located along the optical axis of the line of sight of the user. Positioning the camera along the optical axis of the line of sight of the user may be implemented with a beam splitter. The camera provides the acquired image to processor 208 which detects the alignment or misalignment between reference $230_1$, $230_2$ and $230_3$ and the virtual markers.

According another option for automatic detection, reference points $230_1$, $230_2$ and $230_3$ are light emitters (e.g., markers which include LEDs operated by a small battery, or LEDs connected with a wire to a power supply) detectable by the optical detector in HMD tracking unit 202. The position of reference points $230_1$, $230_2$ and $230_3$ is determined by the user at the beginning of the procedure as described above, or alternatively the position may be automatically determined. For example, the user moves the around patient 226 through at least one position. Each position is associated with a respective viewing angle reference points $230_1$, $230_2$ and $230_3$. For each position, processor 208 determines the P&O of HMD 206 in reference coordinate system 222. Substantially simultaneously therewith, and for each position, the optical detector of HMD tracking unit 202 acquires at least one image of reference points $230_1$, $230_2$ and $230_3$. Processor 208 identifies reference points $230_1$, $230_2$ and $230_3$ in the acquired image and determines position related information respective of each one of reference points $230_1$, $230_2$ and $230_3$ according to the P&O of HMD 206. The position related information includes respective directions toward each of reference points $230_1$, $230_2$ and $230_3$. Each direction defines a line in reference coordinate system 222. The intersection of the at least two lines associated with each reference points $230_1$, $230_2$ and $230_3$ defines the location of that reference point in reference coordinate system 222.

During the procedure, HMD tracking unit 202 acquires an image (i.e., a tracking image employed for tracking) of reference points $230_1$, $230_2$ and $230_3$ (i.e., as well as of light emitter 205 of reference tracking unit 204) and provides the acquired image to processor 208. Also, processor 208 determines an expected location of reference points $230_1$, $230_2$ and $230_3$ in the acquired image according to the P&O of HMD tracking unit 202 and the known position of reference points $230_1$, $230_2$ and $230_3$ in reference coordinate system 222. Processor 208 then identifies and determines the actual location of reference points $230_1$, $230_2$ and $230_3$ in the image acquired by HMD tracking unit 202 (i.e. in the same method used to determine the location of light emitter 205 in the image). When the determined actual location of reference points $230_1$, $230_2$ and $230_3$ in the image corresponds to the expected location of reference points $230_1$, $230_2$ and $230_3$ in the image, processor 208 determines that internal body part 216 and the model thereof are effectively registered. When determined actual location of points $230_1$, $230_2$ and $230_3$ in the image does not correspond to the expected location, processor 208 determines that internal body part 216 and the model thereof are effectively not-registered. Once processor 208 detects effective miss-registration between internal body part 216 and the model thereof, processor 208 may provide an indication (e.g., a visual indication, an audio indication or a tactile indication) to user 214, alerting user 214 that a problem exists and may further aid the user to correct the problem as described above.

According a further embodiment of the disclosed technique, processor 208 detects effective miss-registration between internal body part 216 and the model thereof by employing interrogation camera 211, fixedly attached to HMD 206. Interrogation camera 211 is coupled with processor 208. During the procedure, interrogation camera 211 acquires an image of reference points $230_1$, $230_2$ and $230_3$ (referred to herein as 'interrogation image') and provides the acquired interrogation image to processor 208. Also, since interrogation camera 211 is fixedly attached to HMD 206 in a known P&O relative to HMD tracking unit 202, and processor 208 continuously determines the P&O of HMD 206 in reference coordinate system 222, processor 208 also determines the P&O of interrogation camera 211 in reference coordinate system 222. Processor 208 determines an expected location of reference points $230_1$, $230_2$ and $230_3$ in the interrogation image according to the P&O of interrogation camera 211 and the known position of reference points $230_1$, $230_2$ and $230_3$ in reference coordinate system 222. Processor 208 then employs image processing techniques to identify and determine the actual location of reference points $230_1$, $230_2$ and $230_3$ in the interrogation image. When the determined actual location of reference points $230_1$, $230_2$ and $230_3$ in the image are congruent with (i.e., substantially equal) the expected location of reference points $230_1$, $230_2$ and $230_3$ in the image, processor 208 determines that internal body part 216 and the model thereof are effectively registered. When the determined actual location of points $230_1$, $230_2$ and $230_3$ in the interrogation image are not congruent with the expected location, processor 208 determines that internal body part 216 and the model thereof are effectively not-registered. Once processor 208 detects effective miss-registration between internal body part 216 and the model thereof, processor 208 may provide an indication to user 214, similar to as describe above, alerting user 214 that a problem exist and may further aid the user to correct the problem also as described above. It is noted that in such a case it is not required that the reference points are marked with markers that include LEDs. It is also noted that automatic detection of effective miss-registration as described above cannot detect movement of the HMD relative to the eye of the user.

As mentioned above, the system depicted in FIG. 2 exhibits the in-out-out-in configuration in which reference tracking 204 unit includes one emitter 205 and HMD tracking unit 202 includes two emitters $218_1$ and $218_2$. However, reference tracking unit 204 may include at least two emitters and HMD tracking unit 202 may include one emitter. In general, in the in-out-out-in configuration reference tracking unit 204 includes a reference optical detector and at least one reference emitter and HMD tracking unit 202 includes an HMD optical detector and at least one HMD emitter. In the in-out-out-in configuration, the total number of emitters is at least three. Furthermore, either the HMD tracking system or the tool tracking system or both may be configured to exhibit either the in-out configuration or the out-in configuration. As such, in the in-out configuration, the reference tracking unit includes at least three reference emitters (i.e., similar to reference tracking unit 102—FIG. 1) and HMD tracking unit 202 and tool tracking unit 219 each includes a respective optical detector. In one out-in configuration, the reference tracking unit includes a reference optical detector and HMD tracking unit 202 and tool tracking unit 219 each includes at least three emitters. According to another out-in configuration, one or more optical detectors are placed near the surgical field, such that a clear line-of-sight exists between the optical detectors and the surgical field, and HMD tracking unit 202, tool tracking unit 219 and reference tracking unit 204 include at least three emitters. It is noted that in all the above mentioned configurations, the light emitters may each be a light source or a light reflector. When light reflectors are used a light source is also required, which is typically located adjacent to the optical detectors. It is further noted that if more than one optical detector is used, some of the tracking units may include less than three emitters.

In the example brought forth in FIG. 2, the tracking systems are optical tracking systems based on discrete light emitters. However, other tracking technologies may be employed. For example the tracking system may be based on 3D optical sensors, which in addition to a regular 2D image, also generate a depth image (i.e. for each pixel in the 2D image the 3D sensor determines the distance to the point in the scenery represented by that pixel), such as stereoscopic cameras, a structured-light 3D scanner or a Time-Of-Flight (TOF) camera. The P&O of the tracked object is determined relative to a tracking reference (e.g., a LED or LEDs, track balls, selected features in the scene) the position and orientation of which is substantially constant relative to the body part. The tracking systems may alternatively be magnetic tracking systems or ultrasonic tracking systems. When the tracking system is a magnetic tracking system, HMD tracking unit 202, tool tracking unit 219 and reference tracking unit 204 include receiving coils. A reference tracking unit, which includes a transmitting coil or coils, is placed near the surgical field in a fixed manner relative to the patient and the HMD and the tool are tracked relative to this tracking unit. When the tracking systems are ultrasonic tracking systems, HMD tracking unit 202 and tool tracking unit 219 may include receivers and reference tracking unit 204 may include ultrasonic transmitters the HMD and the tool are tracked relative to this tracking unit. When for example magnetic tracking is employed, the disclosed technique may further provide an indication that the magnetic field according to which tracking is performed has changed (e.g., due to motion of a metallic object). In general, regardless of the tracking technology employ, the P&O of HMD 206 is determined relative to a tracking reference (e.g., a tracking unit or reference feature).

Figure 3:
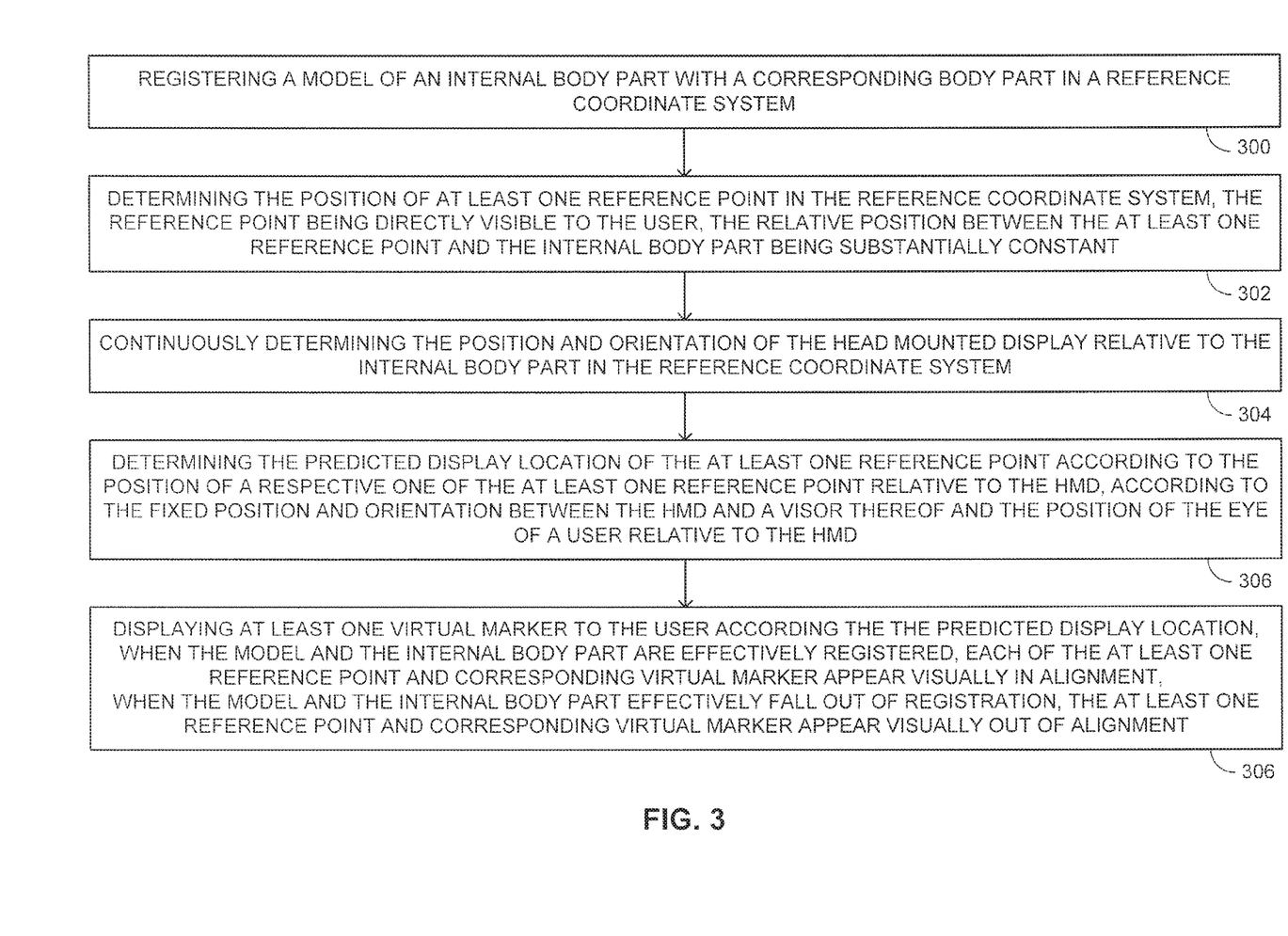
FIG. 3, which is a schematic illustration of a method for verifying registration of a model of an internal body part with the internal body part in a reference coordinate system, in accordance with a further embodiment of the disclosed technique.

Reference is now made to FIG. 3, which is a schematic illustration of a method for verifying registration of a model of an internal body part with the internal body part in a reference coordinate system in accordance with a further embodiment of the disclosed technique. The internal body part is unseen directly by a user. In procedure 300, a model of an internal body part is registered with a corresponding body part in a reference coordinate system. With reference to FIGS. 1C and 1D, model 100 is registered with internal body part 101.

In procedure 302, the position of at least one reference point is determined in the reference coordinate system, the reference point being directly visible to the user, the relative position between the at least one reference point and the internal body part is substantially constant. The reference points may be markings marked by the user or attached to the patient or the treatment bed (e.g., stickers or LEDs). These reference points may be prominent features of a fixture with a substantially fixed spatial relation relative to the body part. The Reference points may further be prominent anatomical features which are directly visible to the user such as the outside corner of the eye, a tooth or the surface of a thigh. The position of the reference points may be determined by placing the tip of a tracked tool on each reference point. Alternatively, the position of the reference points may be determined by viewing each reference point from at least two different directions, where each direction defines a line respective of each reference points and identifying the reference points (i.e., either automatically when the reference points are LEDs or by aiming a cross, which is displayed in the center of the visor, such that the cross aligns with each of reference points). The intersection at least two lines associated with each reference point defines the location of that reference pointe in reference coordinate system. When the reference points are anatomical features such as the corner of the eye or the surface of the thigh, the position of such reference points may be determined, for example, by designating these reference points on acquired image data set. With reference to FIG. 2, processor 208 determines the position of at least one reference point in reference coordinate system 222.

In Procedure 304, the P&O of the HMD is continuously determined relative to the internal body part in the reference coordinate system. With reference to FIG. 2, processor 208 continuously determines the P&O of HMD 206 in reference coordinate system 222.

In procedure 306 the display location of the at least one virtual marker is determined according to the expected position of a respective one of the at least one reference point relative to the HMD, according to the known position and orientation between the HMD and a visor thereof and the position of the eye of a user relative to the HMD. Furthermore, the perspective of the at least one virtual marker is determined. With reference to FIG. 2, processor 208 determines the display location of at least one virtual marker corresponding to a respective at least one reference point.

In procedure 308, at least one virtual marker is displayed to the user (i.e., on the visor of the HMD) according to the determined display location. When the model and the internal body part are registered, each of the at least one reference point and corresponding virtual marker appear visually in alignment. When the model and the internal body part effectively fall out of registration, the at least one reference point and corresponding virtual marker appear visually out of alignment. With reference to FIG. 2, processor 208 renders at least one virtual marker at the expected perspective and display location, and provides the rendered virtual markers to HMD 206. HMD 206 displays the at least one virtual marker to user 214.

Figure 4:
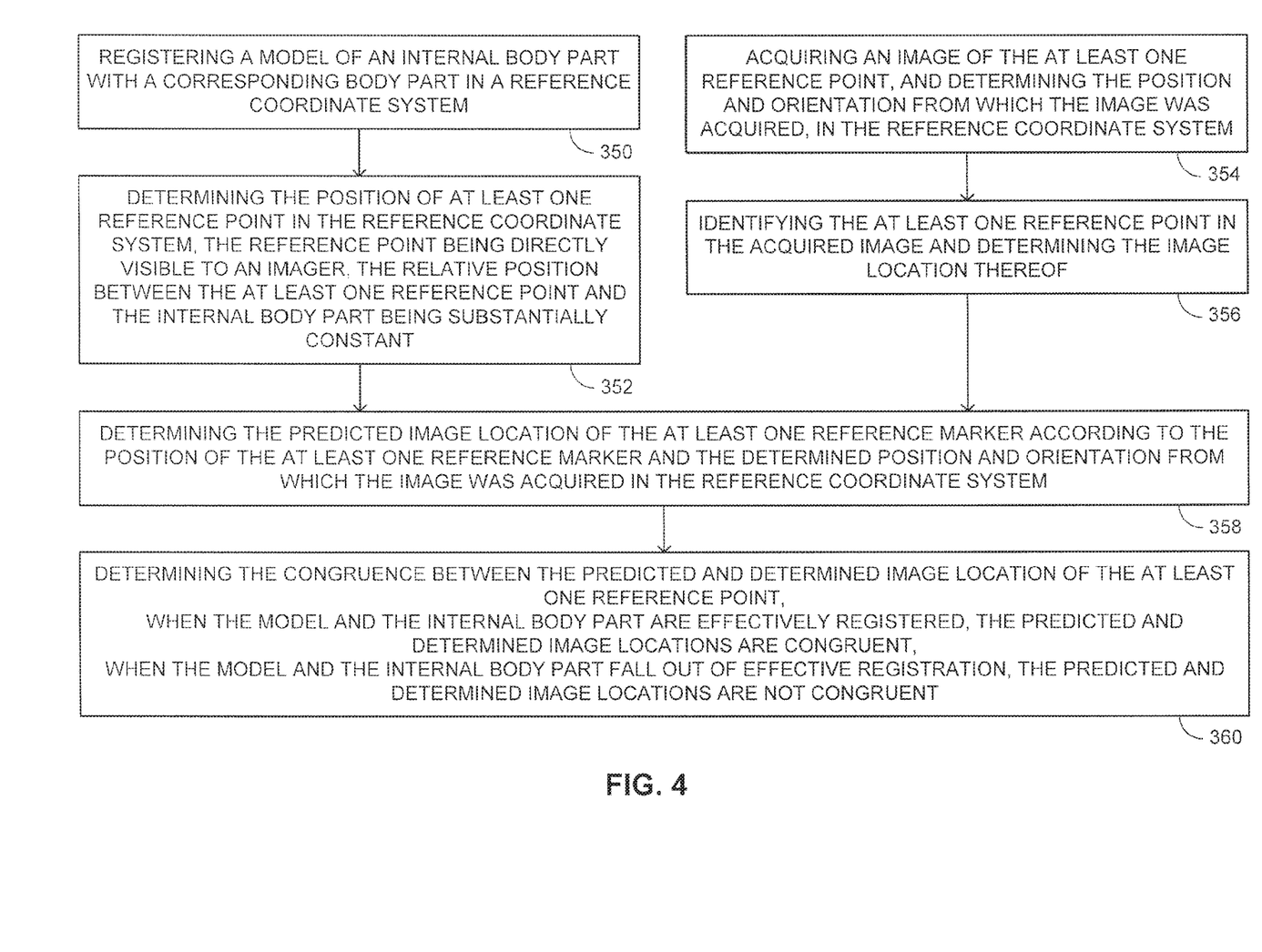
FIG. 4 is a schematic illustration of a method for detecting miss-registration between the internal body part and the model thereof operative in accordance with another embodiment of the disclosed technique.

As mentioned above, effective miss-registration between the internal body part and the model thereof may be detected automatically (e.g., by employing either an interrogation camera or the optical detector of the HMD tracking module). Reference is now made to FIG. 4, which is a schematic illustration of a method for detecting miss-registration between the internal body part and the model thereof operative in accordance with another embodiment of the disclosed technique. The internal body part is unseen directly by a user. In procedure 350, a model of an internal body part is registered with a corresponding body part in a reference coordinate system. With reference to FIGS. 1C and 1D, model 100 is registered with internal body part 101.

In procedure 352, the position of at least one reference point is determined in the reference coordinate system, the reference point being directly visible by an imager, the relative position between the at least one reference point and the internal body part is substantially constant. The reference points may be markings marked by the user or attached to the patient or the treatment bed (e.g., stickers or LEDs). These reference points may be prominent features of a fixture with a substantially fixed spatial relation relative to the body part. The Reference points may further be prominent anatomical features which are directly visible to the user such as the outside corner of the eye, a tooth or the surface of a thigh. The position of the reference points may be determined by placing the tip of a tracked tool on each reference point. Alternatively, the position of the reference points may be determined by viewing each reference point from at least two different directions, where each direction defines a line respective of each reference points and identifying the reference points (i.e., either automatically when the reference points are LEDs or by aiming a cross, which is displayed in the center of the visor, such that the cross aligns with each of reference points). The intersection at least two lines associated with each reference point defines the location of that reference pointe in reference coordinate system. When the reference points are anatomical features such as the corner of the eye or the surface of the thigh, the position of such reference points may be determined, for example, by designating these reference points on acquired image data set. With reference to FIG. 2, processor 208 determines the position of at least one reference point in reference coordinate system 222.

In Procedure 354, an image of the at least one reference point is acquired, and the position and orientation from which the image was acquired is determined in the reference coordinate system. As mentioned above, according to one alternative, the image may be an interrogation image acquired by a dedicated interrogation camera. According to another alternative, when the reference points are marked with light emitters, the image is acquired by the optical detector of the HMD (i.e., a tracking image). With reference to FIG. 2, according to one alternative, interrogation camera 211 acquires an interrogation image of reference points 230$_1$, 230$_2$ and 230$_3$. According to another alternative, when reference points 230$_1$, 230$_2$ and 230$_3$ are light emitters, the optical detector of HMD tracking unit 206 acquires an image of reference points 230$_1$, 230$_2$ and 230$_3$.

In procedure 356, the at least one reference point is identified in the acquired image and the location of the at least one reference point in the image is determined. With reference to FIG. 2, processor 208 identifies the at least one reference point in the acquired image and determines the location thereof in the image.

In procedure 358, the expected location of the at least one reference point in the image is determined according to the position of the at least one reference point in the reference coordinate system and the determined position and orientation from which the image was acquired (i.e., also in the reference coordinate system). With reference to FIG. 2, processor 208 determines the expected location of the at least one reference point in the image.

In procedure 360, the congruence between the expected and determined locations of the at least one reference point in the image is determined. When the model and the internal body part are effectively registered, the expected and determined locations are congruent (i.e., substantially equal) with each other. When the model and the internal body part effectively fall out of registration, the expected and determined image locations are not congruent with each other. With reference to FIG. 2, processor 208 determines the congruence between the expected and determined location of the at least one reference point in the image It will be appreciated by persons skilled in the art that the disclosed technique is not limited to what has been particularly shown and described hereinabove. Rather the scope of the disclosed technique is defined only by the claims, which follow.

The invention claimed is:

1. A method for verifying registration of a model of an internal body part with the internal body part in a reference coordinate system, said model and said internal body part previously registered in said reference coordinate system, said internal body part being at least partially unseen directly by a user, the method comprising the procedures of:
continuously determining a position and orientation of a head mounted display in said reference coordinate system;
determining a display location of at least one virtual marker according to the expected position of a respective at least one reference point relative to said head mounted display, said at least one reference point being directly visible to said user, the position of said at least one reference point in said reference coordinate system is predetermined;
displaying said at least one virtual marker according to said display location,
wherein, when said model and said internal body part are effectively registered, said at least one reference point and said corresponding at least one virtual marker appears visually in alignment,
wherein when said model and said internal body part effectively fall out of registration, said at least one reference point and corresponding virtual marker appear visually out of alignment.

2. The method according to claim 1, further including the procedures of registering said model with said internal body part in said reference coordinate system; and
determining the position of said at least one reference point in said reference coordinate system.

3. The method according to claim 2, wherein said position of said at least one reference point is determined relative to said body part by marking said at least one reference point on said model, when said at least one reference point is visible on said model and directly visible by said user.

4. The method according to claim 2, wherein said position of said at least one reference point is determined relative to said body part by determining the position of a tip of tool in said reference coordinate system when said tip touches each of said at least one reference point.

5. The method according to claim 2, wherein said position of said at least one reference point is determined relative to said body part by determining the position and orientation of said head mounted display while said user designates each one of said at least one reference point from at least two view angles respective of at least two positions of said user.

6. The method according to claim 1, wherein said at least one reference point is one of:
a marking on the skin;
an adhesive marker attached to the skin;
a part of a fixture rigidly attached to said body part; and
an anatomical feature.

7. The method according to claim 1, wherein said model is at least one of:
a one dimensional model;
a two dimensional image;
a three dimensional segmentation based on one of a pre-acquired three dimensional image data and an intra-operative three-dimensional image data;
a volume rendering visualization of one of a pre-acquired three dimensional image data and an intra-operative three-dimensional image data.

8. The method according to claim 7, wherein said two dimensional image is one of a pre-acquired two dimensional image and an intra-operative two dimensional imager.

9. A system for verifying registration of a model of a body part with the internal body part in a reference coordinate system, said model and said internal body part previously registered in said reference coordinate system, said body part being at least partially unseen directly by a user, the system comprising:
a head mounted display to be donned by said user;
a head mounted display tracking module for continuously determining information relating to the position and orientation of said head mounted display in said reference coordinate system; and
a processor, coupled with said head mounted display tracking module, determining the position and orientation of said head mounted display in said reference coordinate system and determining the display location of at least one virtual marker according to the position of a respective at least one reference point relative to said head mounted display, said reference point being visible to said user, the position of said at least one reference point in said reference coordinate system is predetermined, said processor rendering said at least one virtual marker to be displayed on said head mounted display,
wherein, when said model and said body part are effectively registered, said at least one reference point and corresponding virtual marker appear on said head mounted display visually in alignment,
wherein, when said model and said body part effectively fall out of registration, said at least one reference point and corresponding virtual marker appear on said head mounted display visually out of alignment.

10. The system according to claim 9, wherein said processor registers said model with said reference coordinate system, and
wherein said processor determines the position of said at least one reference point.

11. The method according to claim 10, wherein said position of said at least one reference point is determined relative to said body part by marking said at least one reference point on said model, when said at least one reference point is visible on said model and directly visible by said user.

12. The system according to claim 10, wherein said processor determines said position of said of said at least one reference point relative to said body part by determining the position and orientation of said head mounted display while said user designates each one of said at least one reference point from at least two view angles respective of at least two positions of said user.

13. The system according to claim 9, wherein said at least one reference point is one of:
   a marking on the skin;
   an adhesive marker attached to the skin;
   a part of a fixture rigidly attached to said body part; and
   an anatomical feature.

14. The system according to claim 9, wherein said tracking module includes a head mounted display tracking unit and a reference tracking unit,
   wherein, said head mounted display tracking unit being fixedly attached to said head mounted display, and
   wherein said reference tracking unit is fixedly placed relative to said internal body part.

15. The system according to claim 14, wherein said head mounted display tracking unit includes an optical detector and at least one head mounted display light emitter,
   wherein said reference tracking unit includes a reference optical detector and at least one reference light emitter,
   wherein the total number of light emitters is at least three, and
   wherein said reference optical detector acquires at least one image of said at least one head mounted display light emitter and said head mounted display optical detector acquires at least one image of said at least one reference light emitter.

16. The system according to claim 14, wherein said head mounted display tracking unit includes an optical detector, and
   wherein said reference tracking unit includes at least three reference light emitters.

17. The system according to claim 14, wherein said head mounted display tracking unit includes at least three light emitters, and
   wherein said reference tracking unit includes an optical detector.

18. The system according to claim 14, wherein said head mounted display tracking unit and said reference tracking unit each includes at least three light emitters, and
   wherein said tracking module further includes at least one optical detector placed near the surgical field, such that a clear line-of-sight exists between said at least one optical detector and said surgical field.

19. The system according to claim 14, wherein said tracking module further includes a tool tracking unit for determining the position and orientation of a tool.

20. The system according to claim 19, wherein said processor determines said position of said of said at least one reference point relative to said body part by determining the position of a tip of tool in said reference coordinate system when said tip touches each of said at least one reference point.

21. The system according to claim 9, wherein said model is at least one of:
   a one dimensional model;
   a two dimensional image;
   is a three dimensional segmentation based on one of a pre-acquired three dimensional image data and an intra-operative three-dimensional image data;
   a volume rendering of one of a pre-acquired three dimensional image data and an intra-operative three-dimensional image data.

22. The system according to claim 9, wherein said two dimensional image is one of a pre-acquired two dimensional image and an intra-operative two dimensional imager.

23. The system according to claim 9, further including a camera coupled with said processor, said camera acquiring an image from the point of view of the user, said image including representations of said at least one reference point and virtual markers, said camera providing the acquired image to said processor, said processor detecting the alignment or misalignment between said at least one reference point and corresponding virtual marker.

24. A method for verifying registration of a model of an internal body part with the internal body part in a reference coordinate system, said model and said internal body part previously registered in said reference coordinate system, said internal body part being at least partially unseen directly by a user, the method comprising the procedures of:
   acquiring an image of at least one reference point from a known position and orientation in said reference coordinate system;
   identifying the at least one reference point in said acquired image and determining the image location of said at least one reference point, said at least one reference point being directly visible to said user, the position of said at least one reference point in said reference coordinate system is predetermined;
   determining the expected image location of at least one reference point according to the position of said at least one reference point and said position and orientation from which said image was acquired in the reference coordinate system;
   determining the congruence between said predicted and determined image location of said at least one reference point,
   wherein when said model and said internal body part are registered, said predicted and determined image locations are congruent with each other,
   wherein when said model and said internal body part fall out of registration, said predicted and determined image locations are not congruent with each other.

25. The method according to claim 24, further including the procedures of registering said model with said internal body part in said reference coordinate system; and
   determining the position of at least one reference point in said reference coordinate system.

26. The method according to claim 24, wherein said image is one of an interrogation image and a tracking image.

* * * * *